United States Patent [19]

Plattner et al.

[11] Patent Number: 4,510,100

[45] Date of Patent: Apr. 9, 1985

[54] PROCESS FOR THE PRODUCTION OF 2-AMINO-1-NAPHTHALENESULFONIC ACID

[75] Inventors: Eric Plattner, Seltisberg; Sebastian Stäubli, Magden; Fred von Kaenel, Seltisberg, all of Switzerland

[73] Assignee: Ciba Geigy Ag, Basle, Switzerland

[21] Appl. No.: 559,149

[22] Filed: Dec. 7, 1983

Related U.S. Application Data

[63] Continuation of Ser. No. 352,730, Feb. 26, 1982, abandoned.

[30] Foreign Application Priority Data

Dec. 20, 1979 [CH] Switzerland ............... 11315/79

[51] Int. Cl.³ .......................................... C07C 143/60
[52] U.S. Cl. .................................... 260/508; 260/509
[58] Field of Search ........................... 260/508, 509

[56] References Cited

FOREIGN PATENT DOCUMENTS

| 2001637 | 2/1979 | United Kingdom | ............... 260/508 |
| 2001640 | 2/1979 | United Kingdom | ............... 260/508 |
| 2001644 | 2/1979 | United Kingdom | ............... 260/508 |

*Primary Examiner*—Nicky Chan
*Attorney, Agent, or Firm*—Joseph G. Kolodny

[57] ABSTRACT

The invention relates to an improved process for the production of 2-amino-1-naphthalenesulfonic acid (Tobias acid). This improved process makes it possible to obtain Tobias acid which has only a very low content of 2-aminonaphthalene and in high space-time yield. The process starts from 2-hydroxynaphthalene and comprises the following main reaction steps:

(a) the sulfonation of 2-hydroxynaphthalene to 2-hydroxynaphthalene-1-sulfonic acid (oxy-Tobias acid) with chlorosulfonic acid, in an inert organic solvent;

(b) the neutralization of the liberated hydrochloric acid and excess chlorosulfonic acid still present in the reaction medium and conversion of the 2-hydroxynaphthalene-1-sulfonic acid obtained into the corresponding ammonium salt with ammonia;

(c) conversion of the 2-hydroxy group into the 2-amino group by the Bucherer reaction; and (d) the subsequent precipitation of the Tobias acid with dilute sulfuric acid.

7 Claims, 1 Drawing Figure

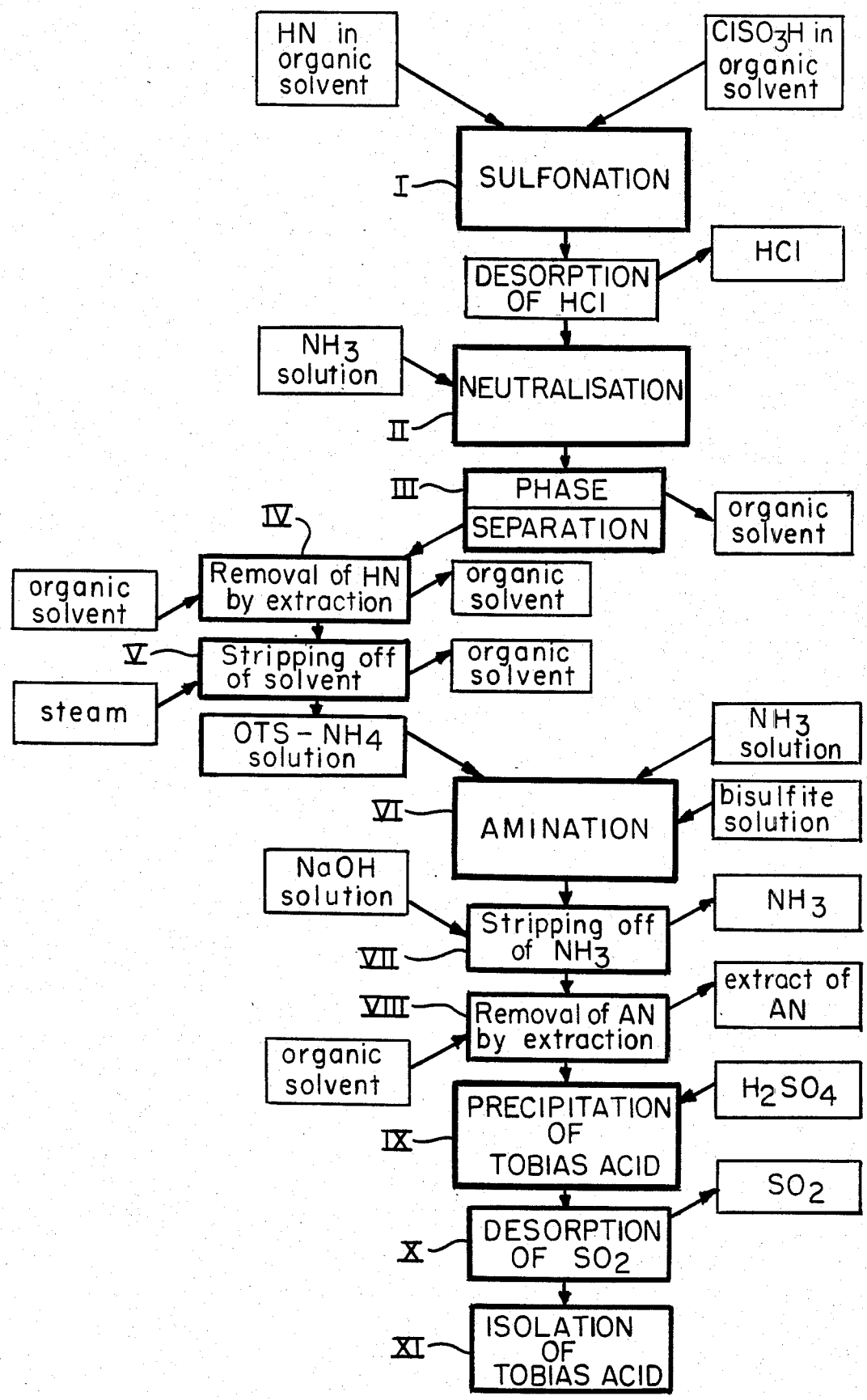

PROCESS FOR THE PRODUCTION OF 2-AMINO-1-NAPHTHALENESULFONIC ACID

This is a continuation of application Ser. No. 352,730, filed Feb. 26, 1982, now abandoned.

The present invention relates to an improved process for the production of 2-amino-1-naphthalenesulfonic acid (Tobias acid). This improved process for the production of Tobias acid makes it possible to obtain a product having a very low content of 2-aminonaphthalene, and is distinguished by high space-time yields.

The process of this invention for the production of Tobias acid starts from 2-hydroxynaphthalene, and comprises the following main reaction steps:

(a) the sulfonation of 2-hydroxynaphthalene to 2-hydroxynaphthalene-1-sulfonic acid, hereinafter referred to as oxy-Tobias acid, with chlorosulfonic acid, in an inert organic solvent (b) the neutralisation of the liberated hydrochloric acid and excess chlorosulfonic acid still present in the reaction medium and conversion of the 2-hydroxynaphthalene-1-sulfonic acid obtained into the corresponding ammonium salt with ammonia;

(c) conversion of the 2-hydroxy group into the 2-amino group by the Bucherer reaction; and (d) the subsequent precipitation of the Tobias acid with dilute sulfuric acid.

The Bucherer reaction is usually employed in the production of Tobias acid by amination of alkali metal salts of 2-hydroxy-1-naphthalenesulfonic acid on an industrial scale. A small number of by-products are formed in this reaction. One of these by-products is 2-aminonaphthalene, which is a carcinogen.

The Occupational Safety and Health Administration (OSHA) has issued regulations which only permit the handling of substances containing 2-aminonaphthalene if the content of this latter is 0.1% by weight or less [see: The Federal Register 39, No. 20, Part III, pp. 3756–3797 (1974) and "The Control of Industrial Bladder Tumours", Scott and Williams, Brit. J. Industrial Medicine 14, pp. 150–163 (1957)]. Tobias acid produced on a large scale has therefore had to be subjected to elaborate aftertreatments in order to meet this requirement, or else production would have had to cease. Surprisingly, it has now been found that Tobias acid containing only very insignificant amounts of 2-naphthylamine, which lie far below the required limits, is obtained by conducting the entire reaction to result in the formation of the more readily soluble ammonium salts instead of the formation of alkali metal salts in the intermediate steps.

The better solubility of the ammonium salt of oxy-Tobias acid permits the batches to be carried out in higher concentrations than with alkali metal salts, whereby—as already mentioned—better space-time yields are obtained and, in connexion therewith, better utilisation of the investment required, of energy, and of ecological measures, to mention only a few advantages.

The production of alkali metal salts of oxy-Tobias acid by sulfonation of 2-hydroxynaphthalene with chlorosulfonic acid is known. Attention is drawn in particular here to U.S. Pat. No. 1,716,082 and Fierz-David and Blangey, "Fundamental Processes of Dye Chemistry" (Interscience Publishers Inc., New York, 1949, pp. 199–200).

The process of U.S. Pat. No. 1,716,082 results in oxy-Tobias acid salts which can be converted by amination into Tobias acid, but the yields of salts are only 85 to 90% of theory and the reaction times of 4 to 6 hours lead to poor space-time yields.

A process for the production of Tobias acid is described in U.S. Pat. No. 2,058,911, which process consists in removing 2-aminonaphthalene by extraction with a water-immiscible organic solvent such as monochlorobenzene or dichlorobenzene, from a product solution obtained in an amination reaction, and acidifying the resultant purified aqueous solution of the sodium salt of Tobias acid until acid to Congo red (pH 3) at a temperature of about 45° C., affording a Tobias acid which is suitable for use as an intermediate for obtaining pigment dyes. This procedure is extremely complicated and leads to losses in yield.

The production of Tobias acid having a low content of 2-naphthylamine also forms the subject matter of German Offenlegungsschriften Nos. 2 831 956, 2 831 965, 2 831 966, 2 831 992, 2 831 993, 2 831 994 and 2 831 995. In these processes, an attempt is made to solve the problem of producing Tobias acid having a low content of 2-naphthylamine by inhibiting the 2-naphthylamine which allegedly forms by decomposition of salts of oxy-Tobias acid or Tobias acid. As in this case too the entire process is concerned with the formation of the less soluble alkali metal salts of oxy-Tobias acid, it has not yet proved possible to find a wholly satisfying solution, especially as regards the space-time yield, which is of such importance for large-scale production.

Accordingly, the present invention has for its object to provide a novel process for the production of 2-amino-1-naphthalenesulfonic acid that does not have the disadvantages of the known processes. This object is accomplished by means of an improved process for the production of 2-amino-1-naphthalenesulfonic acid (Tobias acid), by reacting a suspension of 2-hydroxynaphthalene, in a water-immiscible organic solvent, with chlorosulfonic acid, under anhydrous conditions and in the temperature range from about 0° C. to 10° C., to give 2-hydroxy-1-naphthalenesulfonic acid (oxy-Tobias acid), removing HCl from the reaction mixture by desorption in vacuo and, by addition of aqueous ammonia solution and water, converting the reaction mixture into a two-phase mixture consisting of an organic and an aqueous phase, separating the resultant ammoniacal-aqueous phase and extracting it with a water-immiscible organic solvent to remove 2-naphthol and stripping off the residual organic solvent in the aqueous phase in vacuo, treating the extracted aqueous layer, under pressure, with ammonia and $SO_2$ donors and heating it, stripping off $NH_3$ from the aqueous reaction mixture containing the ammonium salt of Tobias acid thereby obtained and extracting the product solution with a water-immiscible organic solvent, acidifying the extracted aqueous suspension of Tobias acid at elevated temperature, removing $SO_2$ from the suspension by desorption, cooling to 30° C., and collecting the product by filtration, and, if desired, drying it, which process comprises (a) introducing into a suitable reaction vessel, simultaneously and continuously, separate streams of a 20–30% suspension of 2-hydroxynaphthalene in a water-immiscible organic solvent which is inert to chlorosulfonic acid, and of chlorosulfonic acid which may be diluted with the same solvent, in the temperature range from −10° to +10° C., in such concentration and at such a rate of addition that an anhydrous reaction mixture having a molar ratio of chlorosulfonic acid to 2-hydroxynaphthalene of about 0.90 to about 1.05 to 1, preferably 0.95 to 1.05 to 1, is obtained, and leaving the reaction mixture for about 10 to 150 minutes in the reaction vessel, (b) removing HCl from the reaction mixture by desorption under a pressure of 100–400 mbar in the temperature range from 0° to 60° C., preferably from 5° to 15° C., (c) treating the residual reaction mixture for 10 to 60 minutes with an aqueous 25–35% ammonia solution in the temperature range from 40° to 80° C., preferably from 60° to 75° C., until the pH value of the previously acid solution is at least 6 and adding sufficient further water that two liquid phases clearly form, advantageously with at least the same amount of water as of the previously added ammonia solution, subsequently (d) separating the organic solvent phase and the aqueous phase after removal of residual 2-hydroxynaphthalene by extraction with an organic water-immiscible solvent, preferably with the solvent employed in (a), stripping off remaining solvent in vacuo at 200–400 mbar and in the temperature range from 60° to 80° C., (e) treating the resultant ammonium salt of oxy-Tobias acid, without increasing the concentration beforehand, with $NH_3$ and concentrated $(NH_4)_2SO_3$ or $NH_3HSO_3$ solution in the temperature range from 120° to 150° C. and at a pressure of 10 to 20 bar for 4 to 12 hours until the pH value is 9 to 12, and, after stripping off $NH_3$ following an optional prior conversion of the ammonium salt to the alkali metal salt with 20–40% alkali solution in the temperature range from 50° to 80° C. and removal of 2-naphthylamine by extraction with an aromatic hydrocarbon, (f) adding to the reaction mixture, in the temperature range from 30° to 70° C., sufficient dilute 40–60% sulfuric acid to adjust the pH value to 1.2–1.75, removing $SO_2$ from the resultant suspension by desorption in vacuo at 0.1 to 0.9 bar and in the temperature range from 30° to 70° C., and, after cooling to about 30° C., isolating the pure Tobias acid by filtration and, if desired, drying it.

For ecological reasons it is advantageous to treat the ammonium salt of the Tobias acid obtained with alkali before the precipitation with sulfuric acid. The bulk of the ammonia employed in the reaction can thereby be recovered and is accordingly available for recycling.

The following table of the solubilities of the sodium and ammonium salts of oxy-Tobias acid affords clear evidence of the possibility of the better space-time yields which can be obtained by the process of this invention.

Solubility of oxy-Tobias acid in the form of the sodium and ammonium salt in water contingent on the temperature

TABLE 1

| Temp. °C. | Na salt % by weight free acid | $NH_4$ salt % by weight free acid |
|---|---|---|
| 20 | 32.5 | 38.0 |
| 30 | 34.0 | 41.5 |
| 35 | 35.5 | 43.0 |
| 45 | 38.0 | 47.0 |
| 55 | 41.5 | 51.5 |

Water-immiscible organic solvents which are inert to chlorosulfonic acid and are suitable as reaction media for the process of the invention are chlorinated hydrocarbons such as o-dichlorobenzene, monochlorobenzene, but preferably dichloroethane. Suitable extractants for use in the reaction are aromatic hydrocarbons such as toluene, xylenes, or ethylbenzene, as well as the same solvents mentioned above.

A particular advantage of the novel process to be singled out for special mentioned is that the reaction does not have to be initiated from substrates in solution, but from suspensions. As the reaction can be initiated from an approx. 25% suspension of 2-hydroxynaphthalene, it is accordingly possible to use an amount greater by about 60% in the reaction. Owing to shorter reaction times in the succeeding steps and to the better solubility of the ammonium salts, the novel process makes it possible to obtain an approximately 100% better space-time yield compared with prior art processes.

Pure or recycling chlorosulfonic acid is used for the process of the invention in a concentration of about 50% by weight and is diluted with the same solvent in which the 2-hydroxynaphthalene is suspended. Lower concentrations are not suitable on account of loss in space-time yields. Higher concentrations can be used in individual cases.

It is advantageous to use chlorosulfonic acid which is obtained by utilising hydrogen chloride gas which forms during the sulfonation or sulfochlorination with chlorosulfonic acid of e.g. aromatic hydrocarbons such as naphthalene, anthracene or benzene, in an inert organic solvent as reaction medium. Such a hydrogen chloride gas would normally have to be destroyed with considerable expenditure of time and effort, as, depending on the vapour pressure of the organic solvent employed prevailing under the reaction conditions, it contains a greater or lesser amount of this solvent. In order to be able to reuse this impure hydrogen chloride gas, it would first have to be freed from solvent. This would require complicated operations in corrosion-proof apparatus.

The solvent-containing hydrogen chloride gas is reacted with sulfur trioxide, at a temperature below 60° C., in stoichiometric amounts, or in a small excess of hydrogen chloride gas, in chlorosulfonic acid as reaction medium, to give chlorosulfonic acid. As the inert solvents contained in the hydrogen chloride gas are present throughout the entire process, the chlorosulfonic acid obtained contains solvent. It is nonetheless a useful chemical reagent which can be used in sulfonation and sulfochlorination reactions carried out in the same or a similar solvent medium.

Further reagents which are employed are compounds which donate ammonia or ammonia and sulfur dioxide, e.g. aqueous 25–35% ammonia solution or ammonium bisulfite solution.

The novel process is preferably carried out continuously. Although the individual steps are carried out batchwise, a continuous reaction course is achieved by including appropriately dimensioned stack vessels as buffers in the entire process.

In detail, the process of the invention can be carried out e.g. as follows, with reference to the diagram.

The reactants, a 20–30% suspension of 2-hydroxynaphthalene (HN) in an organic solvent which is inert to chlorosulfonic acid, and chlorosulfonic acid which may be diluted with the same organic solvent, are charged separately into storage vessels. The reactants are then fed synchronously from the two storage vessels into an agitator vessel cascade I. The rate of addition is in accordance with the scale of the apparatus and the efficiency of the cooling means, as the reaction is exothermic and a reaction temperature of 0° to 10° C. should be kept. The addition of the reactants must be so synchronised that the molar ratio of chlorosulfonic acid to 2-hydroxynaphthalene is from 0.90 to about 1.05 to 1. The sulfonation is preferably carried out using less than stoichiometric amounts of chlorosulfonic acid with respect to 2-hydroxynaphthalene. The dwell time in this cascade depends on the conditions stated above, and is on average about 70 minutes. The hydrogen chloride gas evolved is exhausted and absorbed or recycled for the fresh production of chlorosulfonic acid as previously described. The hydrogen chloride gas still remaining in solution in the reaction medium is desorbed under a pressure of 100–400 mbar and in the temperature range from 0° to 60° C. The preferred temperature range, however, is from 5° to 15° C. The sulfonation mixture is then fed simultaneously with 25–35% aqueous ammonia solution into the neutralisation and reaction vessel II, the rate of addition being so controlled that a pH value of 6 to 6.5 results. The temperature range in this step is from 40° to 80° C., with the preferred range being from 60° to 75° C. Simultaneously, water is added to the reaction mass in an amount sufficient to form two liquid phases, namely an aqueous product phase and an organic solvent phase which acts as reaction medium. The amount of water, however, depends primarily on the concentration in which it is desired to carry out the remainder of the process. For economic reasons, the concentration of the product mass will be kept as high as possible, i.e. just below the solubility limit of the oxy-Tobias acid (see Table 1). The dwell time in vessel II is from 10 to 60 minutes. The two-phase mixture is then passed into the separating vessel III and, at the same temperature as in vessel II, the organic solvent phase is separated from the aqueous phase. The aqueous phase is freed from remaining unreacted 2-hydroxynaphthalene in a countercorrent extraction column IV using the same solvent as mentioned at the outset. The temperature range in this operation is in the range from 40° to 80° C. After extraction in the stripper V, the solvent remaining in the aqueous phase is distilled off under a pressure of 200–400 mbar and in the temperature range from 60° to 80° C. The aqueous phase then contains the ammonium salt of oxy-Tobias acid as intermediate. At a temperature of about 70° C., The concentration of the dissolved salt is in the range from 50 to 55%. This high concentration procedure leads to very good results in respect of space-time yield and product quality.

The solution of the NH$_4$-salt of oxy-Tobias acid (OTS) is then passed into a reaction column VI. Simultaneously, liquid ammonia and 40–55% NH$_4$SO$_3$ solution are fed into the reactor VI in molar amounts up to an excess of 50%, based on the oxy-Tobias acid salt. The temperature is raised to 130°–150° C., the pressure simultaneously rising to 10–20 mbar. The dwell time in the reactor under these conditions is 4 to 12 hours, on average 8 to 10 hours. The pressure is then reduced and sufficient NaOH solution is added to the reaction mass that all ammonia to be liberated in this manner escapes. The remaining ammonia is stripped off in column VII. The resultant sodium salt of Tobias acid is then diluted to a concentration of 20–30% with water and extracted in the countercurrent extraction column VIII with toluene or a similar aromatic hydrocarbon, in the temperature range from about 60° to 80° C., in order to remove small amounts of 2-aminonaphthalene (AN) still present. The so obtained sodium salt of Tobias acid contains less than 30 ppm of 2-aminonaphthalene.

The pH-controlled precipitation of Tobias acid is then carried out in the vessel IX by simultaneously introducing 40–60% sulfuric acid and reaction mixture in the temperature range from 40° to 70° C., preferably from 45° to 55° C. The amount of acid added is such that a pH value of 1.2 to 1.75, preferably 1.5 to 1.75, results. This operation lasts 20–40 minutes. The SO$_2$ liberated in the course of this operation can be exhausted immediately from the vessel or, alternatively, from the desorption column X, or expelled with an inert gas and recycled to the process for the production of ammonium bisulfite solution. The resultant Tobias acid is collected by filtration on a filter press, washed neutral with water, and dried in vacuo. The yield of Tobias acid obtained by the process of this invention, based on 2-hydroxynaphthalene, is 93–98%.

The Tobias acid obtained by the novel process is a valuable intermediate for the production of dyes. It is used in particular as diazo or coupling component in the production of diazo dyes.

The novel process can be carried out as described in the following Example. It will, of course, be understood that, depending on the concentrations of the different reactants employed, possibilities of varying the process exists.

EXAMPLE

A 22.6% crystalline, readily flowable suspension of β-naphthol in 1,2-dichloroethane is fed at a rate of 1560 g/h (2.44 moles/h) synchronously with 279 g/h (2.39 moles/h) of chlorosulfonic acid into an agitator vessel cascade. The reaction temperature is kept at 0° to 5° C., and the dwell time in the reactor is about 75 minutes.

The hydrogen chloride evolved during the sulfonation is absorbed and that still dissolved in the reaction mass is removed by desorption in vacuo at 0° to 5° C. In an agitator vessel, a 30% ammonia solution is then added continuously to the sulfonation mass at a rate of 145 g/h (2.55 moles/h), at pH 6 to 6.5 and 70°–75° C. The reaction mass is simultaneously diluted with water at a rate of addition of 234 g/h and, after a dwell time of 22 minutes, pumped into a heated separator, where the organic solvent phase is separated from the aqueous product phase at 70°–75° C. The aqueous phase (solution of the ammonium salt of oxy-Tobias acid) is freed from unreacted β-naphthol at the same temperature in a multistage heated countercurrent extraction column with 1,2-dichloroethane at a rate of 1000 g/h. The 1,2-dichloroethane still remaining in the solution of the ammonium salt of oxy-Tobias acid is removed by distillation at about 390 mbar and 70°–75° C. The 1,2-dichloroethane phase containing β-naphthol is extracted with water and recycled after removal of the water. Yield: 1100 g/h of a 51.4% solution of the ammonium salt of oxy-Tobias acid, which is free from dichloroethane and contains about 30 ppm of β-naphthol. The yield of oxy-Tobias acid is 98.3% of theory, based on the β-naphthol employed, up to this phase of the reaction.

1100 g/h of the ammonium salt of oxy-Tobias acid (51.4%), 165 g/h of 100% ammonia and 231 g/h of 54% ammonium bisulfite solution are passed into a reaction column equipped with stirrer and subdivided into chambers. The temperature in the reactor is kept at 140° C. The dwell time is 8.5 hours, and the pressure is adjusted to 15 bar. The oxy-Tobias acid is reacted under these conditions almost completely (>98%) to Tobias acid. After the reaction mixture has passed through the reactor, the pressure is reduced to atmospheric pressure. The reaction mixture is then mixed with aqueous 20% NaOH solution (480 g/h) in order to convert the ammonium salt into the sodium salt. The ammonia is then stripped off in a distillation column and recycled to the reaction. The solution of the product flowing out from the bottom of the column is diluted with water to a concentration of about 250 g of sodium salt of Tobias salt per liter, and extracted continuously with toluene at 70°–75° C. in a countercurrent extraction column. In this manner, 2-naphthylamine is removed from the product solution to an insignificant residual concentration of about 10 ppm with respect to Tobias acid. The free Tobias acid is then precipitated from this solution by addition of 50% sulfuric acid (about 540 g/h), while keeping the temperature at 50°–55° C. and the pH value between 1.5 and 1.75. The $SO_2$ liberated during this operation is desorbed and recycled to the process. The product is collected by filtration, washed with cold water, and dried in vacuo at 70°–75° C. The yield of isolated Tobias acid is 95% of theory, based on oxy-Tobias acid. The concentration of 2-naphthylamine is <30 ppm.

What is claimed is:

1. A process for the production of 2-amino-1-naphthalenesulfonic acid (Tobias acid), which comprises
    (a) introducing into a suitable reaction vessel, simultaneously and continuously, separate streams of a 20–30% suspension of 2-hydroxynaphthalene in a water-immiscible organic solvent which is inert to chlorosulfonic acid, and of chlorosulfonic acid which may be diluted with the same solvent, in the temperature range from $-10°$ to $+10°$ C., in such concentration and at such a rate of addition that an anhydrous reaction mixture having a molar ratio of chlorosulfonic acid to 2-hydroxynaphthalene of about 0.90 to about 1.05 to 1 is obtained, and leaving the reaction mixture for about 10 to 150 minutes in the reaction vessel to give 2-hydroxy-1-naphthalenesulfonic acid (oxy-Tobias acid),
    (b) removing HCl from the reaction mixture by desorption under a pressure of 100–400 mbar in the temperature range from 0° to 60° C.,
    (c) treating the residual oxy-Tobias acid containing reaction mixture for 10 to 60 minutes with an aqueous 25–35% ammonia solution in the temperature range from 40° to 80° C. until the pH value of the previously acid solution is at least 6, to get the ammonium salt of the oxy-Tobias acid and adding sufficient further water that two liquid phases clearly form, subsequently,
    (d) separating the organic solvent phase from the aqueous phase and after removal of residual 2-hydroxynaphthalene by extraction with an organic water-immiscible solvent, stripping off remaining solvent from the aqueous phase in vacuo at 200–400 mbar and in the temperature range from 60° to 80° C.,
    (e) treating the resultant aqueous solution of the ammonium salt of oxy-Tobias acid, without increasing the concentration beforehand, with $NH_3$ and concentrated $(NH_4)_2SO_3$ or $(NH_4)HSO_3$ solution in the temperature range from 120° to 150° C. and at a pressure of 10 to 20 bar for 4 to 12 hours until the pH value is 9 to 12, to give the ammonium salt of 2-amino-1-naphthalenesulfonic acid (Tobias acid), and, after stripping off $NH_3$ and removal of 2-naphthylamine by extraction with an aromatic hydrocarbon,
    (f) adding to the reaction mixture, in the temperature range from 30° to 70° C., sufficient dilute 40–60% sulfuric acid to adjust the pH value to 1.2–1.75, removing $SO_2$ from the resultant suspension by desorption in vacuo at 0.1 to 0.9 bar and in the temperature range from 30° to 70° C., and, after cooling to about 30° C., isolating the pure Tobias acid by filtration and, if desired, drying it.

2. A process according to claim 1, which comprises diluting the chlorosulfonic acid in step (a) with the same solvent as is used for the extraction of 2-hydroxynaphthalene, carrying out the desorption of HCl in step (b) in the temperature range from 5° to 15° C., carrying out the formation of the ammonium salt of oxy-Tobias acid in step (c) in the temperature range from 60° to 75° C. and, after the addition of ammonia, adding at least the same amount of water as of the previously added ammonia for better phase separation, extracting the aqueous phase in step (d) with the same solvent as is used in step (a), and, in step (e), before stripping off the ammonia, converting the ammonium salt of Tobias acid into the alkali metal salt to recover the ammonia by addition of 20–40% aqueous alkali solution, in the temperature range from 50° to 80° C.

3. A process according to claim 1, wherein the water-immiscible organic solvent which is inert to chlorosulfonic acid is monochlorobenzene, dichlorobenzene, dichloroethane or tetrachloroethane.

4. A process according to claim 1, wherein the solvent used for extraction is an aromatic hydrocarbon.

5. A process according to claim 1, wherein the sulfonation in step (a) is carried out with less than the stoichiometric amount of chlorosulfonic acid, based on 2-hydroxynaphthalene.

6. A process according to claim 1 which comprises, in step (a), introducing into an agitator vessel cascade, simultaneously and continuously, separate streams of reactants consisting of a 23% suspension of 2-hydroxynaphthalene in 1,2-dichloroethane and chlorosulfonic acid diluted with the same solvent, in the temperature range from 0° to 5° C., in such concentration and at such a rate of addition that an anhydrous reaction mixture with a molar ratio of chlorosulfonic acid to 2-hydroxynaphthalene of about 0.95 to 1 is obtained, and leaving the reaction mixture from about 70 minutes in the reaction vessel, in step (b) removing hydrogen chloride from the reaction mixture by desorption under a pressure of 100–400 mbar and in the temperature range from 5° to 10° C., in step (c) adding a 23–25% ammonia solution to the reaction mixture over the course of 10 to 60 minutes, and in the temperature range from 60° to 75° C., until the pH of the previously acid solution is at least 6, and diluting the reaction mixture with at least the same amount of water as of the previously added ammonia solution, in step (d) separating the organic solvent phase and the aqueous phase after removal of the remaining ammonia by extraction with 1,2-dichloroethane, and stripping off remaining solvent from this phase under a pressure of 200–400 mbar in the temperature range from 60° to 80° C., in step (e) treating the ammonium salt of oxy-Tobias acid, without increasing the concentration beforehand, with liquid $NH_3$ and concentrated $NH_4HSO_3$ solution in the temperature range from 120° to 150° C. and at a pressure of 10 to 20 bar over the course of 8 to 10 hours until the pH value is 9–11, and, after stripping off NH$_3$ following conversion of the ammonium salt into the alkali metal salt by addition of 20–40% alkali solution in the temperature range from 50° to 80° C., and removing 2-naphthylamine by extraction with toluene, in step (f) simultaneously adding the reaction mixture, in the temperature range from 45° to 55° C., to sufficient dilute 40–60% sulfuric acid that a pH value of 1.5 to 1.75 results, removing SO$_2$ from the resultant suspension by desorption in vacuo at 0.1 to 0.5 bar and in the temperature range from 45° to 55° C. and, after cooling to about 30° C., isolating the pure Tobias acid by filtration, and washing and drying it.

7. A process of claim 4 wherein the aromatic hydrocarbon is toluene, xylene or ethyl benzene.

* * * * *

UNITED STATES PATENT AND TRADEMARK OFFICE
CERTIFICATE OF CORRECTION

PATENT NO. : 4,510,100

DATED : April 9, 1985

INVENTOR(S) : Eric Plattner, et al

It is certified that error appears in the above-identified patent and that said Letters Patent is hereby corrected as shown below:

Col. 5, line 47          Delete "The" and substitute --the--

Col. 8, line 48          After "mixture" delete "from" and substitute --for--

Signed and Sealed this

Twenty-seventh Day of August 1985

[SEAL]

Attest:

DONALD J. QUIGG

Attesting Officer      Acting Commissioner of Patents and Trademarks